United States Patent [19]
Fernie

[11] Patent Number: 5,860,437
[45] Date of Patent: Jan. 19, 1999

[54] SELF-CLEANING HAND WASHER

[75] Inventor: Geoffrey Roy Fernie, Etobicoke, Canada

[73] Assignee: CSIA Research Foundation, North York, Canada

[21] Appl. No.: 692,226

[22] Filed: Aug. 7, 1996

[51] Int. Cl.⁶ ...................................................... B08B 3/02
[52] U.S. Cl. ..................... 134/95.2; 134/95.3; 134/99.2; 134/104.1; 134/104.2; 134/200
[58] Field of Search .................. 134/95.2, 95.3, 134/99.2, 104.1, 104.2, 200; 604/289

[56] References Cited

U.S. PATENT DOCUMENTS

| | | |
|---|---|---|
| 2,641,771 | 6/1953 | Schiro . |
| 3,699,984 | 10/1972 | Davis . |
| 3,918,987 | 11/1975 | Kopfer ................................... 134/95.2 |
| 4,219,367 | 8/1980 | Cary . |
| 4,670,010 | 6/1987 | Dragone ................................... 604/289 |
| 4,817,651 | 4/1989 | Crisp . |
| 5,074,322 | 12/1991 | Jaw ...................................... 134/200 X |
| 5,193,563 | 3/1993 | Melech . |
| 5,265,628 | 11/1993 | Sage et al. ........................ 134/104.1 X |

Primary Examiner—Philip R. Coe
Attorney, Agent, or Firm—Philip C. Mendes da Costa; Bereskin & Parr

[57] ABSTRACT

A hand washing apparatus and having a hand washing bowl mounted at a suitable height for washing the hands, the bowl being moveable between open and closed positions, controls for moving the bowl between a hand washing position and an inactive position, a dispenser for dispensing warm water over the hands in the bowl, a dispenser for dispensing soap over the hands in the bowl, and, a dispenser for dispensing rinse water over the hands in the bowl. Also disclosed is a method of cleansing the hands using such apparatus.

25 Claims, 6 Drawing Sheets

SELF-CLEANING HAND WASHER

FIELD OF THE INVENTION

The invention relates to hand washing machines, and in particular to a self-contained hand washing machine which is self-cleaning and disinfecting between each usage and which incorporates disinfected air for drying the hands in a clean atmosphere.

BACKGROUND OF THE INVENTION

Washing of the hands is believed to be one of the first safeguards against spreading infection, whether in a health care institution, or in any other facility or location. However, the facilities which are usually provided for hand washing are to say the least somewhat primitive, and have scarcely changed in design since plumbing was first introduced. Most hand washing facilities are based on a basin, with hot and cold water taps, and a source of soap. Drying of the hands is at best dependent on disposable paper towels, or in many cases by hot air hand dryers.

Disposable paper towels frequently do not get rid of all of the residue from washing. Disposal of the towels may result in recontamination of the hands. Hot air drying of the hands uses small appliances with fans and electrical heating coils. These appliances when brand new work reasonably well, simply blowing fresh air over the hands. However, after even a small amount of usage contaminated air is drawn into the air hand dryer and bacteria accumulate in the warm, moist atmosphere in the dryer. The result is that from then on the hands are dried in air which may be carrying a substantial volume of bacteria.

Even the multiple washing of the hands many times does not overcome these problems.

A further problem is that the sink or basin in which the washing water is collected itself becomes a source of contamination after only a very few usages. Dirt and dried soap collect, and breed bacteria in the basin itself.

The operation of the handles on the faucets is itself yet another source of contamination. Persons may turn the faucets on and off, for example, after relieving themselves, when their hands are actually contaminated, and thereby leaving contamination on the handles of the faucets. For all of these reasons, therefore, the use of conventional hand washing facilities, even those in health care institutions, is unsatisfactory and unhygienic and may actually result in the spreading of infection and bacteria, rather than the reverse.

Clearly, it is desirable to provide a hand washing facility in which, the hands do not touch the basin, taps or soap dispenser, and in which the water is mixed to the correct temperature automatically so that taps do not have to be operated.

In the present embodiment the basin is automatically closed by rotating the basin into an in use sealed position and back into an out of use position between uses, so that it cannot become contaminated by persons tossing garbage. However the bowl can be uncovered, for use and covered when not in use, by means other than rotating the bowl, if desired. The soap is dispensed automatically and does not accumulate as a residue, and the basin is rinsed and dried after each use. The air for drying the hands is disinfected continuously.

Preferably the entire washer is operated by a foot pedal, or other means remote from the basin, and not requiring contact with the hands.

The cycle of operations is preferably controlled by automatic controls and timers, so that no input is required from the user.

The entire washer unit is self-contained and self-operating, requiring only regular maintenance by qualified trained personnel.

Accumulation of dried soap residue is avoided by careful design of the soap and water dispensers.

In some cases, hand drying aids such as towels can be provided for use in conjunction with the warm air drier.

The entire washer is of such a compact unitary design that it can be installed almost anywhere, not merely in bathrooms. In this way, more frequent washing of the hands is encouraged, and the unit will maintain a clean, attractive appearance without daily maintenance.

BRIEF SUMMARY OF THE INVENTION

With a view to providing an improved hand washing apparatus, the invention comprises a hand washing apparatus in turn comprising, a hand washing bowl mounted at a suitable height for washing the hands, said bowl being moveable between a covered and uncovered position, means for dispensing water, at a controlled temperature, over the hands in the bowl, together with a controlled amount of soap, or disinfecting mixture, over the hands in the bowl, and, means for dispensing rinse water over the hands in the bowl, and means for drying the hands after rinsing.

The invention further provides a hand washing apparatus wherein said inactive position of said bowl renders said bowl inaccessible, so as to avoid collection of contamination.

The invention further provides a hand washing apparatus wherein said bowl is of generally hemispherical shape and is swingably mounted, and wherein, in said hand washing position, is open upwardly, for access by a user, and when in said inactive position, is rotated into a closed position wherein the interior of said bowl is sealed and inaccessible.

The invention further provides a hand washing apparatus including air drying means for generating a stream of hot air flowing over the hands, said air drying means being automatically operable after completion of said rinsing of said hands by said rinse water.

The invention further provides a hand washing apparatus wherein an air stream is further adapted to flow around the interior of said bowl when said bowl is rotated into its inactive position, for drying the bowl.

The invention further provides a hand washing apparatus including means for discharging a disinfectant fluid into said bowl when said bowl is in its inactive position, for flowing around the interior of said bowl and rendering the same clean.

The invention further provides a hand washing apparatus wherein said hot air stream is further adapted to flow around the interior of said bowl when said bowl is rotated into its inactive position.

The invention further provides a hand washing apparatus including a collection sink arranged around said bowl, and whereby when said bowl is rotated into its inactive position, the liquid contents of said bowl are discharged into said sink as waste.

The entire apparatus is self-contained within a closed housing for security and cleanliness.

The various features of novelty which characterize the invention are pointed out with more particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

DESCRIPTION OF A SPECIFIC EMBODIMENT

Figure 1:
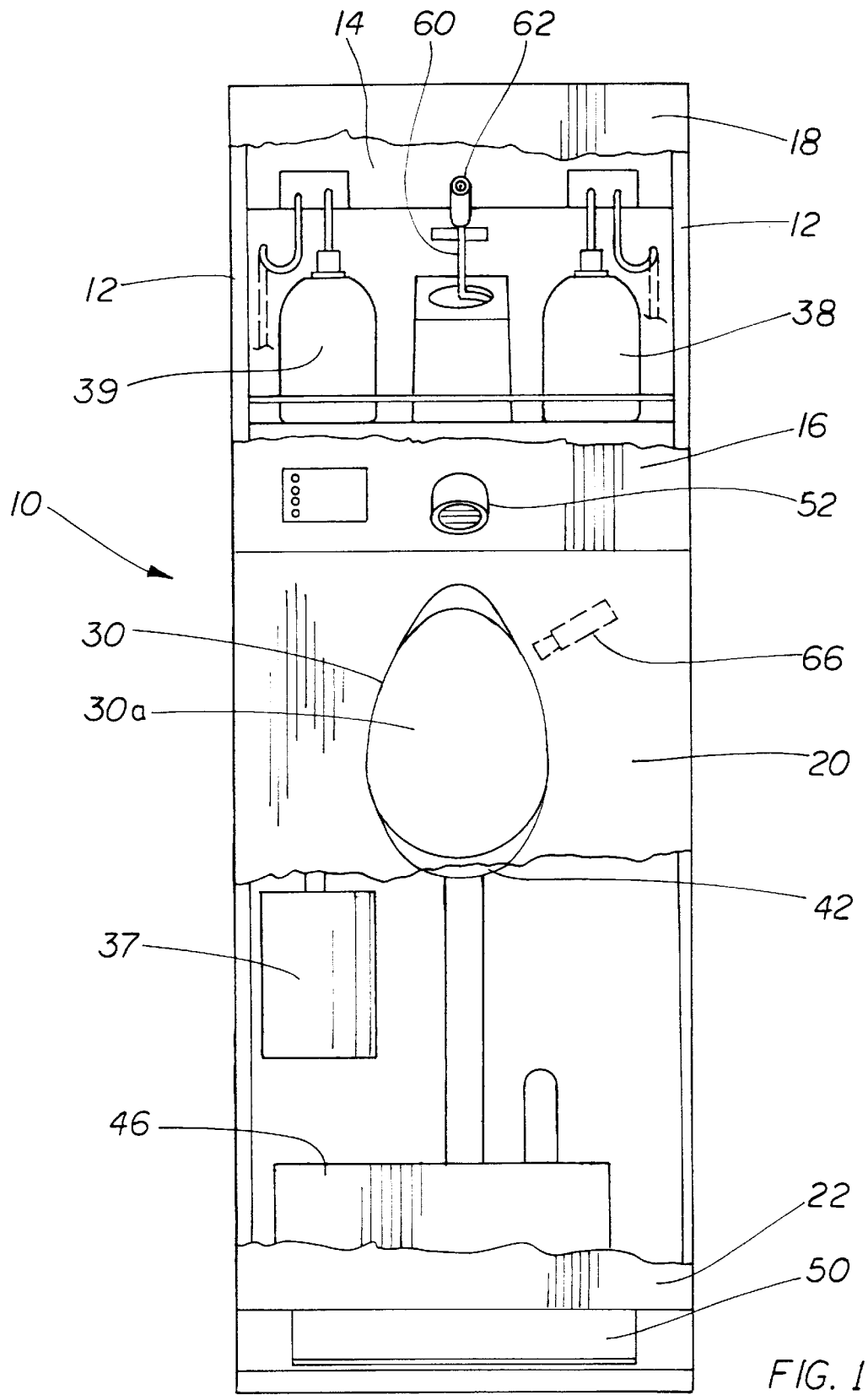
FIG. 1 is a front elevational view of the hand washing machine in accordance with the invention, with the front removed so as to show various parts of the interior.
Figure 2:
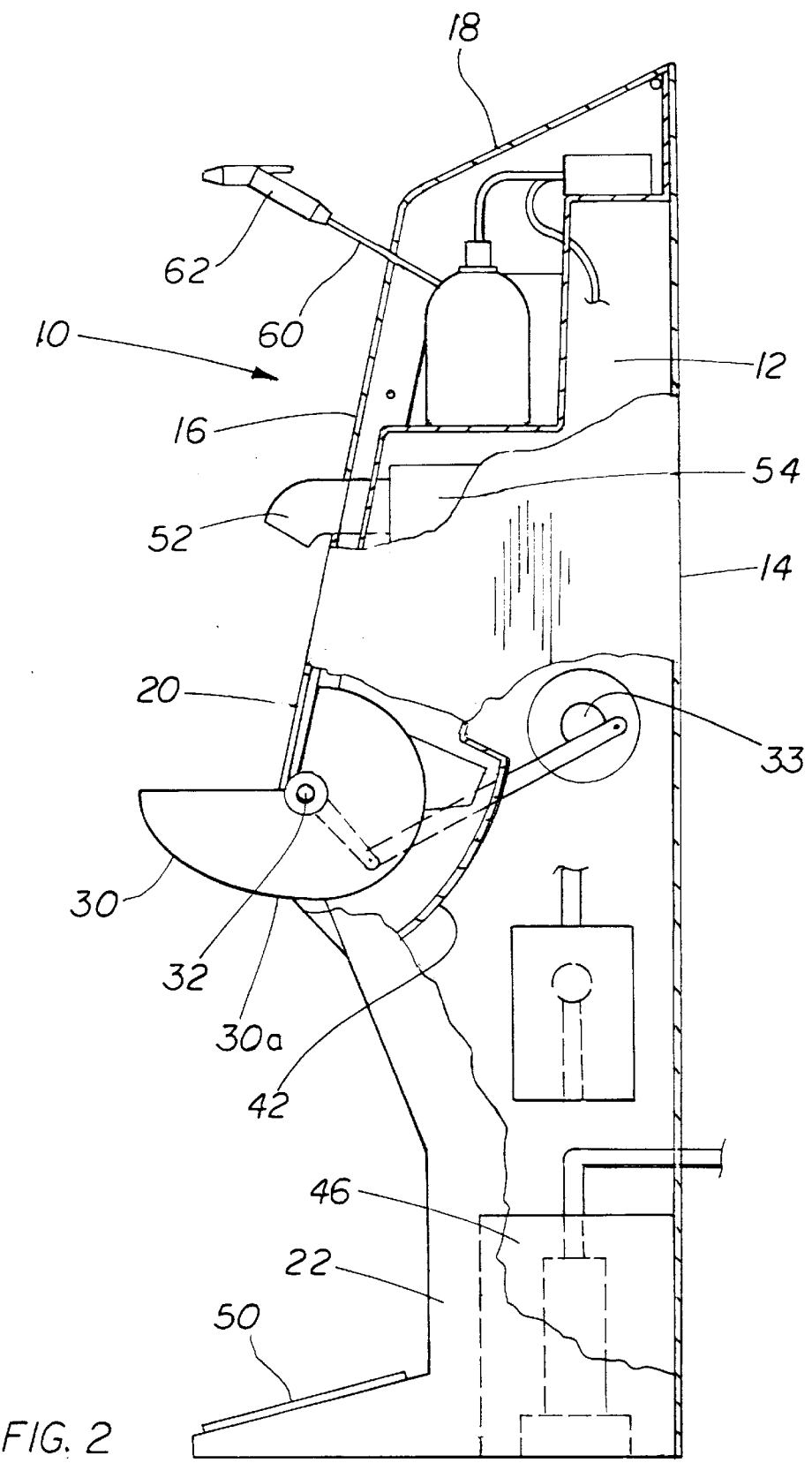
FIG. 2 is a side elevational view partly in section showing a person washing his hands.

FIGS. 1 and 2 illustrate a hand washer demonstrating the various features of the invention, and comprising a generally rectangular upright housing 10, having sidewalls 12-12 and a back wall 14. A contoured front wall 16 defines a roof 18, and forwardly projecting washing region 20. A recessed foot region 22 is defined at the lower end of front wall 16.

Figure 3:
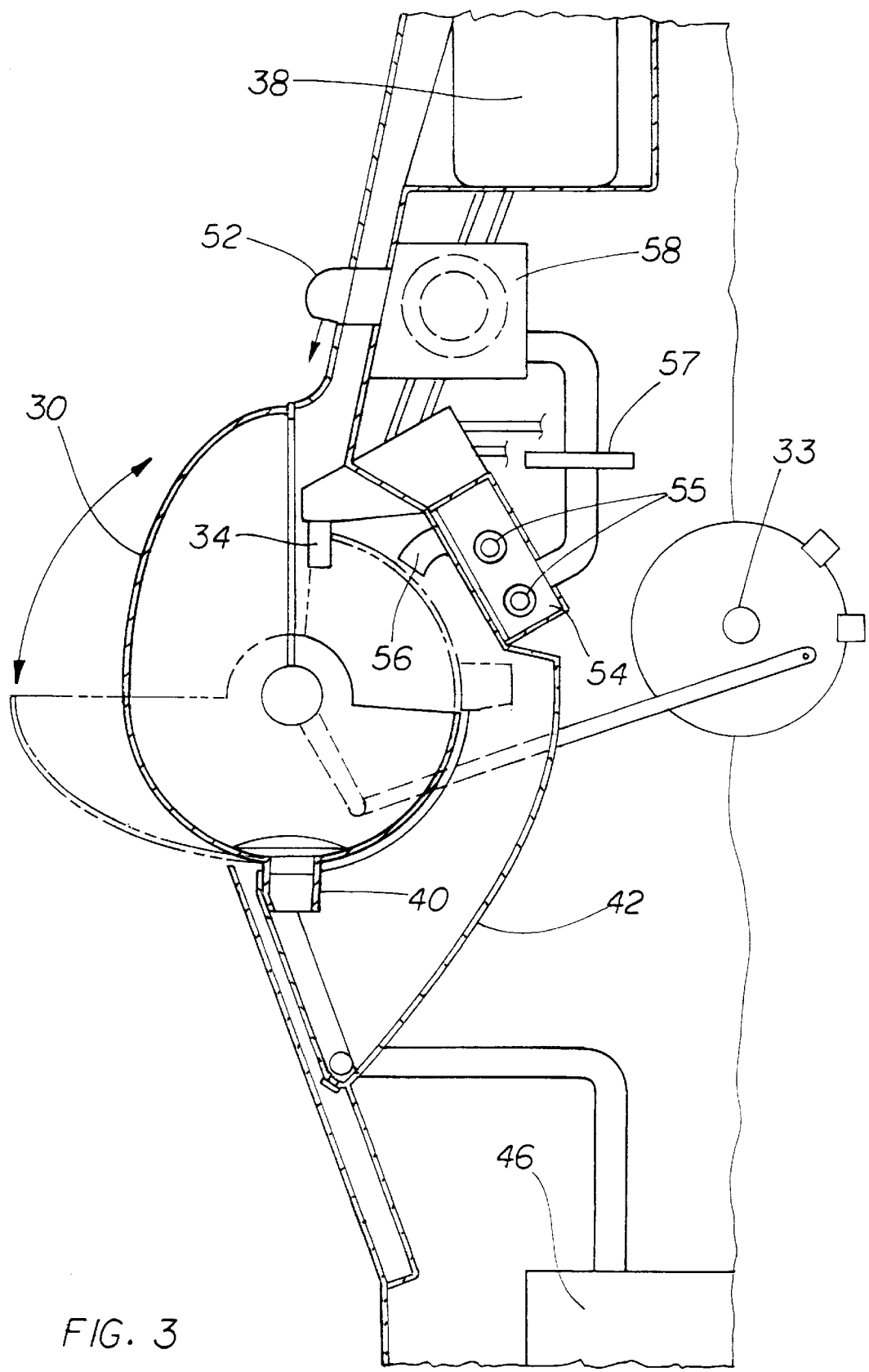
FIG. 3 is an enlarged sectional view corresponding to FIG. 2 showing the basin portion rotated inwardly for rinsing and disinfecting.
Figure 4:
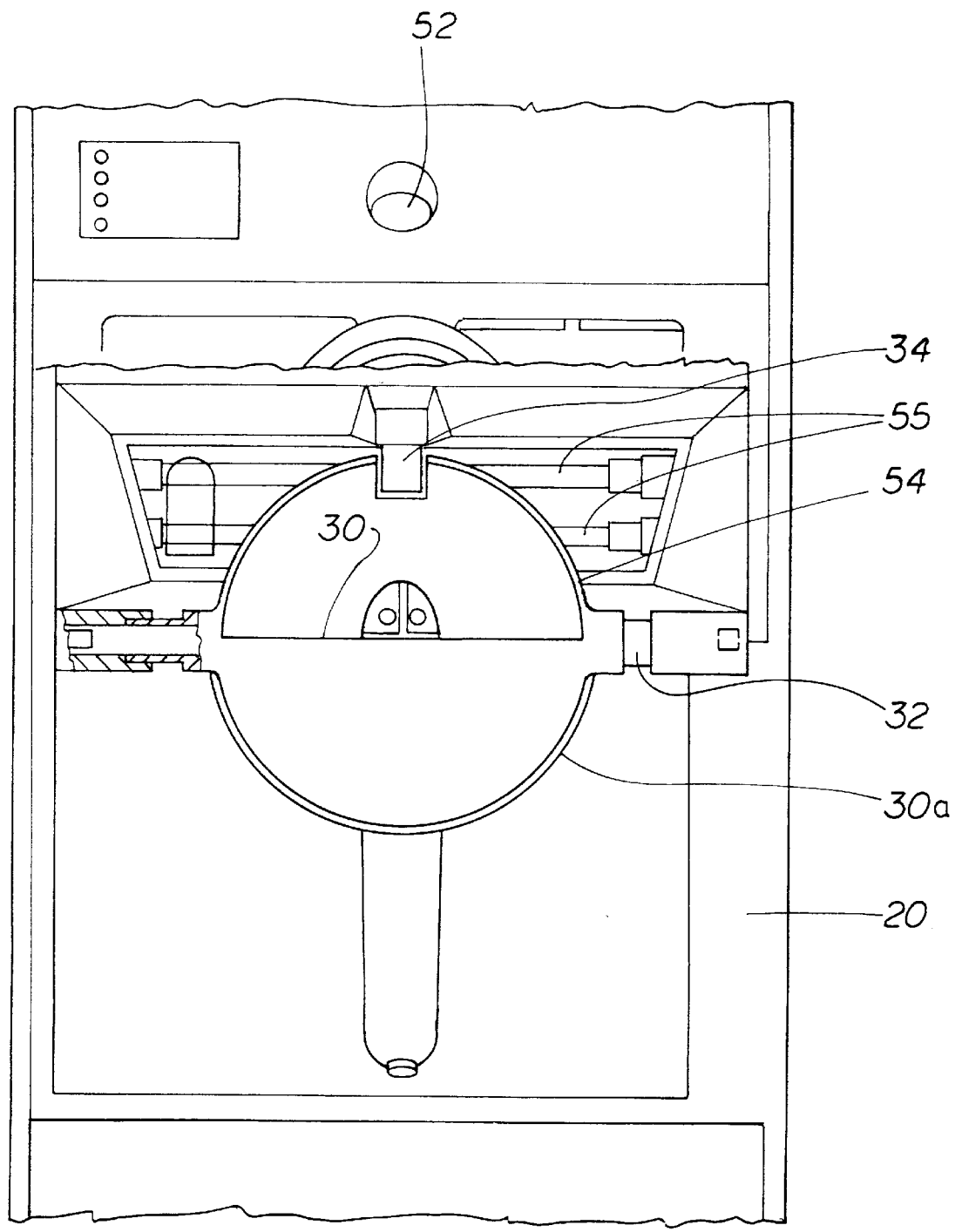
FIG. 4 is an enlarged front elevation of the bowl, swinging forwardly.

Within the front wall 16, on suitable framework the details of which are omitted for the sake of clarity, there is a hand washing bowl indicated generally as 30, which is pivotally mounted along a generally horizontal pivot axis by means of bearings 32. In this way the bowl or sink 30 can be rotated to open outwardly for washing (FIG. 2) and rearwardly into a covered inactive position for rinsing and disinfecting (FIG. 3) by suitable motor and crank means 33.

The bowl 30 is of generally semi-spherical shape, and, when rotated rearwardly (FIG. 3) the underside 30A of the bowl presents a smooth generally convex appearance, effectively closing and sealing the interior of the entire apparatus and preventing contamination by garbage or debris or personal contamination.

While the bowl is described as being rotatably mounted other forms of moveable mounting are possible. Thus, the bowl could simply slide in and out. The bowl could have a cover which moves to cover or uncover the bowl.

Located to one side of the bowl, within the interior enclosed by front wall 16, is a water outlet indicated generally as 34. Nozzle 34 is adapted to direct water at a suitable temperature in a manner to be described into the bowl 30 for wetting of the hands.

Water may be supplied by a pump (not shown), or simply by using the main's water pressure through a pressure regulator and a suitable water/soap mixing valve 36. Valve 36 is connected to a supply of cold water, and connected to a water heater 37 contained within the apparatus, and controllable so as to supply warm water mix at an appropriate temperature. Also connected to the nozzle 34 is a soap container 38, by means of which soap or disinfectant may be supplied to the nozzle 34 for mixing with the controlled temperature water at an appropriate concentration of soap or disinfectant to water.

Also connected to the nozzle 34 is a disinfectant liquid material supply from a tank 39.

Bowl 30 has a rearwardly directed drain spout 40, for discharge of its contents, when it is rotated rearwardly.

In order to catch the washing water and residue, and also the disinfectant, from the bowl 30, the bowl 30 is in turn mounted over a sink 42, which is fixed within the interior of front wall 16, and is connected by a conventional plumbing waste pipe 44 to a sump 46.

In this way, when the bowl 30 is rotated rearwardly, it will dump all of its contents through spout 40 into sink 42 and down the waste pipe 44. The water mixer, soap container 38 and disinfectant container 40 and their pumps are all connected through suitable timing mechanism, so as to provide a timed operation for washing, namely, an initially wetting of the hands, followed by a soaping of the hands, followed by a rinsing of the hands in rinse warm water. At this point the bowl will then rotate rearwardly.

The bowl 30 is then cold cleaned by water which is supplied to the mixing valve 36 by the mains, receiving cold water from the conventional cold water supply together with a disinfectant, for washing and cleaning the bowl. Hot water could be used if desired. The washing mixture will drain out of the bowl 30 through spout 40, into sink 42. The bowl then is directed by air being drawn from outside.

The entire operation of the bowl 30 and the water and soap dispenser is initiated by means of a foot operated pedal 50 (FIG. 2) so that the hands do not touch any of the controls, either before or after washing and rinsing.

In order to dry the hands, a hot air dryer nozzle 52 is provided (FIG. 1).

Hot air nozzle 52 is connected so as to supply heated and disinfected air. For this purpose an air disinfecting chamber 54 is provided with ultraviolet light tube 55. Air is drawn inwardly around bowl, 30 and through nozzle 56 then through a suitable filter 57 and heater and fan 58 before exiting at the nozzle 52.

Nozzle 52 and the fan (not shown) are timed to supply sufficient hot air for the drying of the hands after rinsing.

In this way, not only are the hands thoroughly cleaned and washed without contact with any part of the apparatus, but they are also dried and disinfected by disinfected air.

With the bowl 30 rotates rearwardly it is then rinsed and disinfected, and is itself dried by the outside air, drawn in from atmosphere, by nozzle 56 rendering it dry and clean for the next user. If desired, this drying air could also be disinfected and/or heated.

From time to time it may be desirable for service personnel to wash down the entire unit. For this purpose a flexible hose 60 is provided having a manually operable jet nozzle 62, and connected to the water supply within the apparatus through a suitable valve 64 designed to be operable only by the service personnel, for preventing vandalism and abuse.

Figure 5:
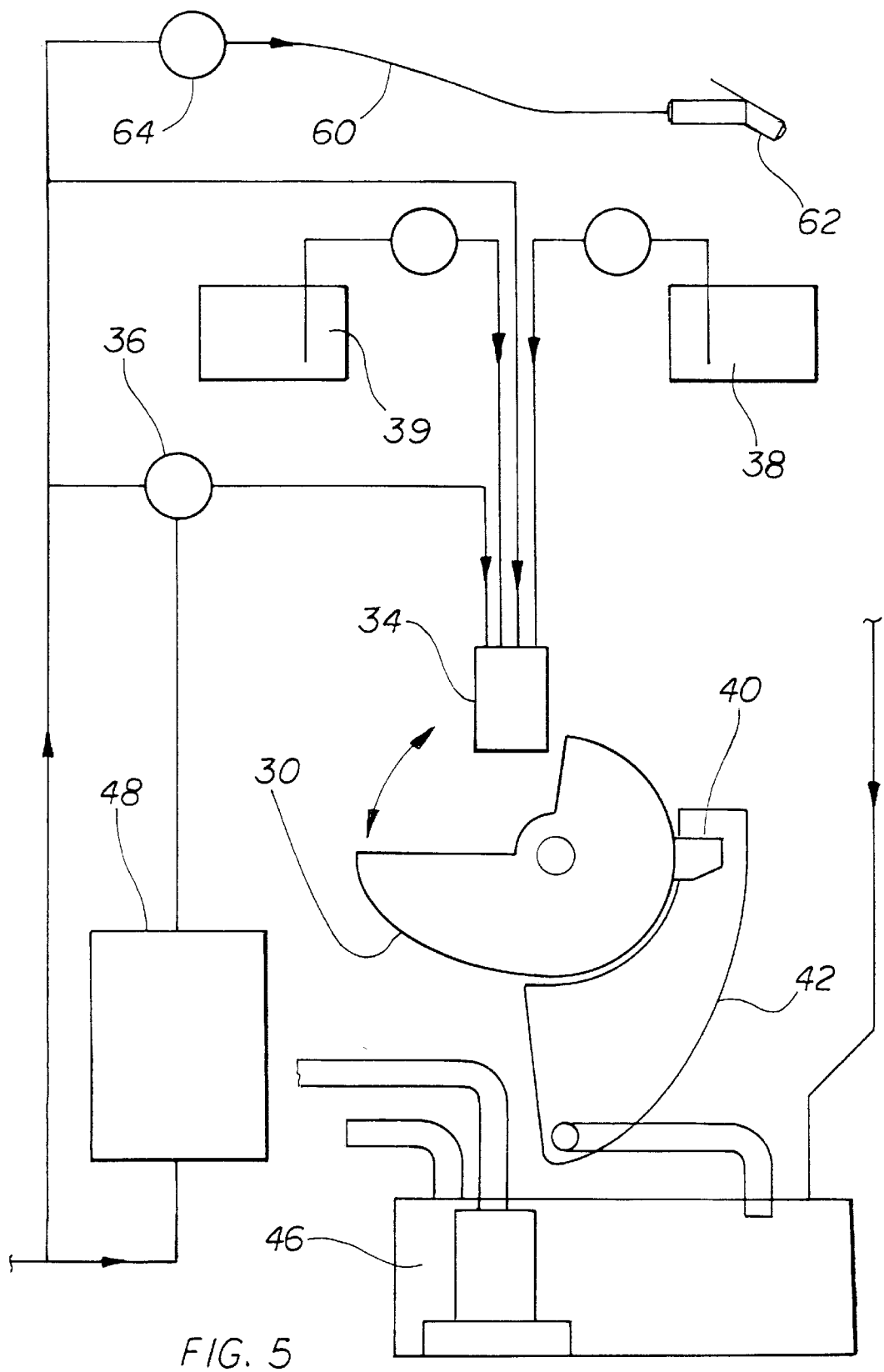
FIG. 5 is a plumbing diagram showing the water inflow and outflow routing.

It will of course be appreciated that there are a large number of detailed electrical connections and controls and valves and relays. However, reference to the plumbing diagram FIG. 5 and the block diagram FIG. 6 will clarify the major operations of the apparatus, and be a sufficient explanation for persons skilled in the art to understand the design and construction of the apparatus.

Finally, reference may be made to a safety feature of the invention, consisting of a light sensitive device 66, which senses the presence of a person's hands in the vicinity of the bowl 30 when it is open. This safety lamp prevents reverse rotation of the bowl 30, so long as the person's hands are still in the vicinity of the bowl 30, thereby preventing a possible injury. It also illuminates the hands so that a person can check for cleanliness.

Figure 6:
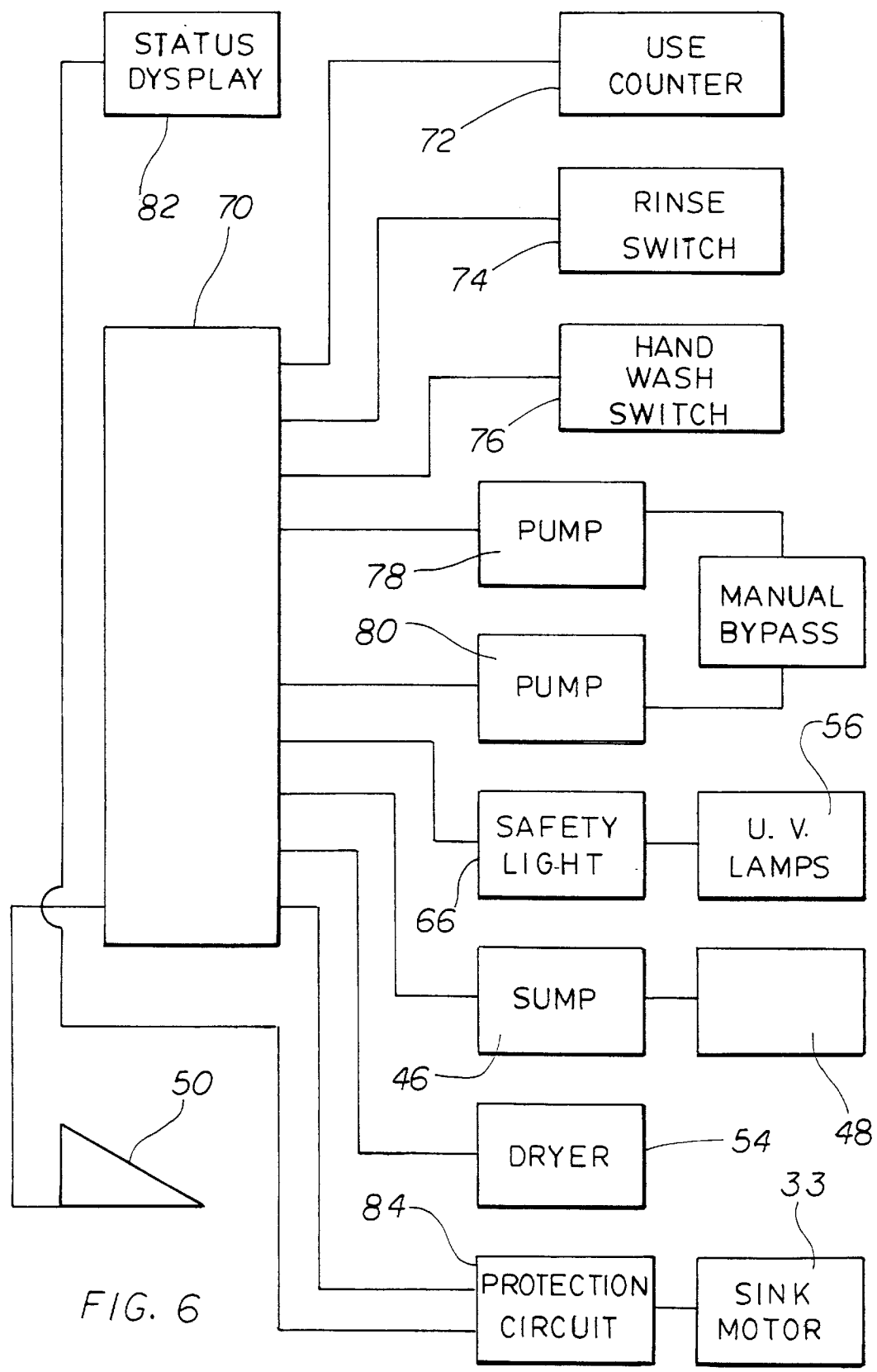
FIG. 6 is an electrical block diagram showing the basic controls, and their relation to the foot switch.

FIG. 6 will be seen to indicate a main controller 70, operated by means of the foot switch 50, and connected to a use counter 72, a rinse switch 74, a hand wash solenoid 76. It is also connected to two pumps 78 and 80 and to a bowl operation protection device 66 already referred to and the ultraviolet light tube 56, and to the dryer operation 54.

Within the sump or reservoir 46, a pump 48 is provided, to periodically empty the sump. The reservoir can also be connected o the main plumbing drainage if desired.

A status display 82, is connected to the controller via the protection circuit 84, so as provide a visible display of the operative status of the apparatus.

The operation of the whole apparatus is self-evident from the foregoing description.

In the inoperative condition, the bowl 30 is normally rotated rearwardly, so that the hemispherical underside of the bowl is directed outwardly, thereby rendering the entire apparatus secure, and sealed all around the bowl.

A user wishing to use the apparatus will first of all operate the foot control, and the sequence of operations will then be started as follows:

A. Bowl rotates open.

B. Clean, water at the controlled temperature is dispensed over the hands.

C. A cleansing solution of water and soap or other disinfectant is then mixed with the water and then dispensed over the hands and the hands are washed.

D. A rinsing solution of water at the controlled temperature is then dispensed over the hands and the hands are rinsed clean.

E. The hands are then withdrawn from the bowl and the bowl 30 rotates closed, dumping the washing water into the sink 42, where it flows under gravity to the sump tank.

F. A hot-air jet is then directed over the hands, having been first of all passed through the ultraviolet chamber to disinfect the air.

During this time while the hands are in the bowl, the bowl is prevented from closing, inadvertently, by the safety light.

G. Water and disinfectant mixture is then sprayed around the interior of the bowl, while it is closed to disinfect the interior of the bowl. Air is drawn in around the bowl to dry it. In some cases this air may be first disinfected and heated, as described.

If desired, air, either hot or cold, can be directed around the side areas of the front panel on the side of the bowl, and also around the floor next to the foot pedal to dry any moisture that may have escaped.

The counter 72 will record usage. The counter may even identify the actual user through suitable remote sensing techniques.

After an appropriate count of uses, maintenance personnel will then check the apparatus, clean it and wash it down, and refill the various containers.

The apparatus will be seen to provide both an effective disinfected means of cleaning the hands, without contacting other contaminants, and in which the cleaning water is operated automatically, the soap dispenser is operated automatically without manual control and in which the bowl itself is cleansed and disinfected between each usage, so that there is no need for the hands to touch anything, after which the hands are dried by disinfected hot air. The whole operation as far as the user is concerned is controlled by means of a foot pedal thereby removing further sources of contamination common to conventional hand cleaning facilities.

The controlling of a washing cycle is designed to meet the various codes, such as FDA requirements. The invention controls the sequence of events, the timing and duration, temperatures, the solution mixes, the cleaning of the bowl, and the drying of the hands, as well as recording the successful completion of this sequence.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A hand washing apparatus comprising:
   a hand washing bowl mounted at a suitable height for washing hands, said bowl being mounted for rotation about a generally horizontal axis between a hand washing position and an inactive position;
   a controller for rotating said bowl between said hand washing position and said inactive position;
   a warm water dispenser for dispensing warm water over hands in the bowl;
   a soap dispenser for dispensing soap over hands in the bowl; and
   a rinse water dispenser for dispensing rinse water over hands in the bowl.

2. A hand washing apparatus as claimed in claim 1 and wherein said inactive position of said bowl renders said bowl inaccessible, so as to avoid collection of externally introduced contamination.

3. A hand washing apparatus as claimed in claim 1 and wherein said bowl is of generally hemispherical shape, and wherein, in said hand washing position, is open upwardly, for access by a user, and when in said inactive position, is rotated into a closed position wherein the interior of said bowl is inaccessible.

4. A hand washing apparatus as claimed in claim 1 including an air dryer for generating a stream of hot air flowing over the hands, said air dryer being automatically operable after completion of said rinsing of said hands by said rinse water.

5. A hand washing apparatus as claimed in claim 4 wherein said hot air is disinfected prior to flowing over the hands.

6. A hand washing apparatus as claimed in claim 1 including a discharger for discharging a disinfectant fluid into said bowl when said bowl is in its inactive position, for flowing around the interior of said bowl and rendering the same clean.

7. A hand washing apparatus as claimed in claim 6 wherein an air stream is further adapted to flow around said bowl when said bowl is rotated into its inactive position and cleaned, for drying the bowl.

8. A hand washing apparatus as claimed in claim 1 including a collection sink arranged around said bowl, and whereby when said bowl is rotated into its inactive position, the liquid contents of said bowl are discharged into said sink as waste.

9. A hand washing apparatus comprising:
   a hand washing bowl mounted at suitable height for washing hands;
   a controller for opening said bowl into a hand washing position and closing said bowl into an inactive position;
   a warm water dispenser for dispensing warm water over hands in the bowl;
   a soap dispenser for dispensing soap over hands in the bowl; and,
   a rinse water dispenser for dispensing rinse water over hands in the bowl.

10. A hand washing apparatus as claimed in claim 9 and wherein said inactive position of said bowl renders said bowl inaccessible, so as to avoid collection of contamination.

11. A hand washing apparatus as claimed in claim 9 including an air dryer for generating a stream of hot, disinfected air flowing over the hands, said air dryer being automatically operable after completion of said rinsing of said hands by said rinse water.

12. A hand washing apparatus as claimed in claim 11 including a discharger for discharging a disinfectant fluid into said bowl when said bowl is in its inactive position, for flowing around the interior of said bowl and rendering the same clean.

13. A hand washing apparatus as claimed in claim 12 wherein said hot air stream is further adapted to flow around the interior of said bowl when said bowl has been cleaned.

14. A hand washing apparatus comprising:

a housing;

a hand washing bowl mounted at a suitable height on said housing for washing hands, said bowl being moveable relative to said housing;

a controller for moving said bowl between a hand washing position and an inactive position;

a dispenser for dispensing warm water and soap and rinse water over the hands in the bowl;

a drain for removing the water from the bowl; and, means for cleaning the bowl after washing.

15. A hand washing apparatus as claimed in claim 14 and wherein said inactive position of said bowl renders said bowl inaccessible, so as to avoid collection of contamination.

16. A hand washing apparatus as claimed in claim 14 including an air dryer for generating a stream of disinfected hot air flowing over the hands, said air drying means being automatically operable after completion of said rinsing of said hands by said rinse water.

17. A hand washing apparatus as claimed in claim 14 including a discharger for discharging a disinfectant fluid into said bowl when said bowl is in its inactive position, for flowing around the interior of said bowl and rendering the same clean.

18. A hand washing apparatus as claimed in claim 17 wherein an air stream is adapted to flow around said bowl when said bowl has been cleaned, to dry the bowl.

19. A hand washing apparatus as claimed in claim 14 including at least one drain located in said bowl, whereby the liquid contents are discharged as waste, when in the inactive position.

20. A hand washing apparatus comprising:

a housing;

a hand washing bowl mounted at a suitable height on said housing for washing hands, said bowl being moveable between an exposed position and a covered position;

a dispenser for dispensing warm water, soap and rinse water over hands in the bowl; and a foot operated controller for controlling movement of said bowl between said exposed position and said covered position, and controlling said dispensing means.

21. A hand washing apparatus as claimed in claim 20 and wherein said bowl in said exposed position,is open upwardly, for access by a user, and when in said covered position, is closed wherein the interior of said bowl is inaccessible.

22. A hand washing apparatus as claimed in claim 20 including an air dryer for generating a stream of disinfected hot air flowing over the hands.

23. A hand washing apparatus as claimed in claim 20 including a discharger for discharging a disinfectant fluid into said bowl when said bowl is in its covered position, for flowing around the interior of said bowl and rendering the same clean.

24. A hand washing apparatus as claimed in claim 23 wherein an air stream is adapted to flow around said bowl when said bowl is cleaned, to dry said bowl.

25. A hand washing apparatus as claimed in claim 20 including a drain connected with said bowl whereby the liquid contents of said bowl are discharged as waste.

* * * * *